United States Patent [19]

Takano et al.

[11] Patent Number: 5,789,425
[45] Date of Patent: Aug. 4, 1998

[54] IMIDAZOLIDINONE DERIVATIVES, THEIR ACID ADDUCTS AND THERAPEUTIC DRUGS FOR SENILE DEMENTIA

[75] Inventors: Yasuo Takano, Kazo; Masanori Takadoi, Kuki; Kei Okazaki, Nogi-machi; Takashi Hirayama, Washimiya-machi; Atsuhiro Yamanishi, Nogi-machi, all of Japan

[73] Assignee: Kyorin Pharmaceutical Co., Ltd., Tokyo, Japan

[21] Appl. No.: 612,829

[22] PCT Filed: Sep. 12, 1994

[86] PCT No.: PCT/JP94/01506

§ 371 Date: Mar. 15, 1996

§ 102(e) Date: Mar. 15, 1996

[87] PCT Pub. No.: WO95/07906

PCT Pub. Date: Mar. 23, 1995

[30] Foreign Application Priority Data

Sep. 17, 1993 [JP] Japan .................. 5-254985
Sep. 9, 1994 [JP] Japan .................. 6-241931

[51] Int. Cl.$^6$ .................. A61K 31/445; C07D 401/06; C07D 401/04
[52] U.S. Cl. .................. 514/341; 546/274.1; 546/274.4
[58] Field of Search .................. 546/274.1, 274.4; 514/341

[56] References Cited

U.S. PATENT DOCUMENTS

| | | |
|---|---|---|
| 4,073,911 | 2/1978 | Huebner . |
| 4,329,348 | 5/1982 | Huebner . |
| 4,600,430 | 7/1986 | Abdulla et al. |
| 5,300,515 | 4/1994 | Takano et al. |

FOREIGN PATENT DOCUMENTS

| | | |
|---|---|---|
| 0 268 229 | 5/1988 | European Pat. Off. |
| 1 441 440 | 6/1976 | United Kingdom . |

OTHER PUBLICATIONS

Chemical Abstracts, vol. 104, No. 23, pp. 757, Jun. 9, 1986, AN–207273c, & Chemical Abstracts, Chemical Substances, vol. 96–105, pp. 33975CS, 1982–1986, RN–102224–01–1.

Journal of Organic Chemistry, vol. 26, No. 10, 4051–4057, Oct. 24, 1961, "The Rearrangement and Cyclization of Ethyl N–(Methylaminoalkyl) Carbanilates and 1,1-Dimethyl–3–Methylaminoalkyl—3–Phenylureas", W.B. Wright et al.

Methoden Der Organischen Chemie, Houben–Weyl, vol. E4, pp. 377–380, 1983, "Kohlensäure–Derivate", K.H. Büchel, et al.

*Primary Examiner*—Patricia L. Morris
*Attorney, Agent, or Firm*—Oblon, Spivak, McClelland, Maier & Neustadt, P.C.

[57] ABSTRACT

Imidazolidinone derivatives represented by a following general formula (1) or pharmacologically permissible acid addition salts with cholinergic activity (muscarine $M_1$ activity) provide compounds useful for the therapy of senile dementia.

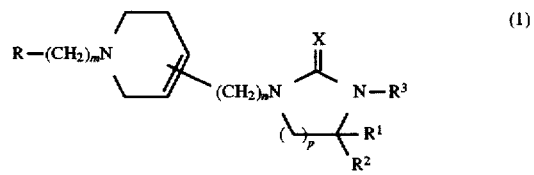

(1)

(wherein R denotes a lower alkyl group which may be substituted by halogen, or the like, $R^1$ and $R^2$ denote identically or differently hydrogen atoms or lower alkyl groups, $R^3$ denotes a formula

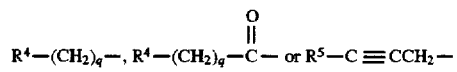

(wherein $R^4$ denotes a lower alkyl group which may be substituted by halogen, or the like, q denotes 0 to 3, and $R^5$ denotes a hydrogen atom or the like), m and n denote 0 to 3, p denotes 1 to 3, and X denotes an oxygen atom or sulfur atom).

4 Claims, No Drawings

IMIDAZOLIDINONE DERIVATIVES, THEIR ACID ADDUCTS AND THERAPEUTIC DRUGS FOR SENILE DEMENTIA

TECHNICAL FIELD

The present invention relates to imidazolidinone derivatives with cholinergic activity (muscarine $M_1$ activity) or pharmaceutically acceptable acid addition salts, processes for preparing them and therapeutics for senile dementia having them as effective components.

BACKGROUND TECHNIQUES

In recent years, as the average span of life becomes long, the senile dementia such as Alzheimer type senile dementia has posed a significant problem both medically and socially.

The patients of dementia show symptom such as loss of intellectual ability, disturbance of memory, disturbance of abstract thinking, verbal aphasia, apraxia, disorientation, etc. and the disorder of basic functions lies in the disturbance of the formation of memory or the expressive ability of retained memory. Until today, however, there have been almost no medicaments that can treat this effectively, hence immediate development of therapeutic drugs is desired.

It is said that the disturbances of learning and memory in the patients of dementia (in particular, senile dementia and Arzheimer type senile dementia) are particularly associated with the decrease in central cholinergic function. Hence, such compounds that have this central cholinergic function, that is, the functional activity of acetylcholine being a nerve transmitter can be used for the treatment of patients of dementia (Science, 217, 408 (1982): R. I. Bartus et al.).

It is said that, among the degenerative diseases of nerve due to decreased central cholinergic function, the core symptoms relating particularly to the disturbances of memory, recognition, etc. are due to the decreased function of central cholinergic nerve and conventionally, for improving these core symptoms, administration of acetylcholinesterase inhibitor such as physostigmine, administration of acetylcholine precursors such as choline and lecithin, administration of drugs acting on the cholinergic receptor such as arecoline, and the like have been attempted (e.g. Dementia, 1, 188 (1987) etc.). All of these attempts however have many problematic points that they are ineffective in the therapy, that, even if slight effect may be developed, adverse effect is strong or the therapeutic range is narrow, and the like.

The purpose of the invention is to provide the therapeutic drugs for senile dementia which activate the central cholinergic function of the patients of dementia (in particular, senile dementia and Arzheimer type senile dementia) and which are effective for the therapy of the disturbance of memory and having high safety, taking the present status of the patients of dementia aforementioned into consideration.

DISCLOSURE OF THE INVENTION

As a result of diligent studies searching for the therapeutics particularly for the disturbance of memory among various symptoms of dementia for the purpose of developing novel therapeutics for senile dementia, the inventors have found that the inventive imidazolidinone derivatives and their acid adducts have excellent cholinergic activity (muscarine $M_1$ activity).

Namely, according to the invention, it has been found that imidazolidinone derivatives represented by a general formula (1)

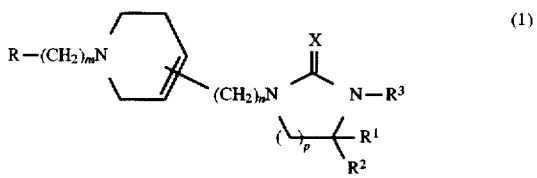

(1)

(wherein R denotes a lower alkyl group which may be substituted by halogen, cyclic alkyl group, or phenyl group, naphthyl group, 5-membered or 6-membered hetero ring and its benzene-condensed ring which may have one or more substituents, $R^1$ and $R^2$ denote identically or differently hydrogen atoms or lower alkyl groups, $R^3$ denotes a formula

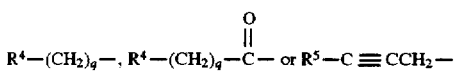

(wherein $R^4$ denotes a lower alkyl group which may be substituted by halogen, cyclic alkyl group, or phenyl group, naphthyl group, 5-membered or 6-membered hetero ring and its benzene-condensed ring which may have one or more substituents, q denotes 0 to 3, and $R^5$ denotes a hydrogen atom or formula

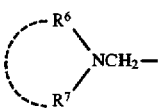

(wherein $R^6$ and $R^7$ denote identically or differently lower alkyl groups or may form a ring together with nitrogen atom (further may contain one hetero atom), m and n denote 0 to 3, p denotes 1 to 3, and X denotes an oxygen atom or sulfur atom), or their acid addition salts have surprisingly excellent choline functional activity (muscarine $M_1$ activity) and that additionally they have antiamnesia effect, leading to the completion of the invention.

The compounds represented by this general formula (1), that is, compounds with tetrahydropyridine ring substituted into imidazolidinone ring are novel compounds in structure. Moreover, these compounds have said excellent effect and yet are compounds with low toxicity.

In the description of the general formula (1) of the invention, for "cyclic alkyl group", ones with carbon atoms of 3 to 7 such as cyclopropyl, cyclopentyl and cyclohexyl are mentioned, for "lower alkyl", straight chain or branched ones with carbon atoms of 1 to 6 such as methyl, ethyl, n-propyl and isopropyl are mentioned, and, for "substituents" in "phenyl group, naphthyl group, 5-membered or 6-membered hetero ring and its benzene-condensed ring which may have one or more substituents", halogen atom, lower alkyl group, lower alkoxy group, lower alkylthio group, lower alkoxycarbonyl group, nitro group, amino group, cyano group, etc. are mentioned.

For "halogen atom", fluorine, chlorine, bromine and iodine are mentioned, for "lower alkoxy", straight chain branched ones with carbon atoms of 1 to 4 such as methoxy, ethoxy and propoxy are mentioned, for "lower alkoxycarbonyl group", methoxycarbonyl, ethoxycarbonyl, etc. are mentioned, and "amino group" may be substituted by acyls, for example, acetyl etc. or may be substituted by one or two lower alkyl groups.

"Hetero ring" in "5-membered or 6-membered hetero ring and its benzene-condensed ring" is a saturated or unsaturated monocyclic or polycyclic heterocyclic group capable of containing one or more nitrogen, oxygen and sulfur atoms, and, for example, piperidyl, piperazyl, morpholyl, furanyl, thienyl, pyrrolidyl, pyrazolyl, imidazolyl, oxazolyl, thiazolyl, pyridyl, pyrimidyl, pyridazyl, pyrazyl, etc. are mentioned. For "its benzene-condensed ring", benzofuranyl, benzothienyl, indolyl, benzimidazolyl, benzoxazolyl, benzothiazolyl, quinolyl, isoquinolyl, quinazolyl, quinoxalyl, cinnolyl, etc. are mentioned.

"To form a ring together with nitrogen atom (further may contain one hetero atom)" is a saturated monocyclic heterocyclic group capable of additionally containing one nitrogen, oxygen or sulfur atom, and, for example, pyrrolidyl, piperidyl, piperazyl, morpholyl, etc. are mentioned.

For "eliminating group", halogen atoms, lower alkylsulfonyloxy group, arylsulfonyloxy group, etc. are mentioned.

"Acid addition salts" are pharmaceutically acceptable salts with, for example, hydrochloric acid, citric acid, succinic acid, fumaric acid, maleic acid, etc.

The inventive compounds represented by a general formula (2) can be prepared through, for example, two kinds of preparative processes shown below (A and B).

[A] The compounds represented by the general formula (1) can be synthesized by reacting compounds represented by the general formula (2)

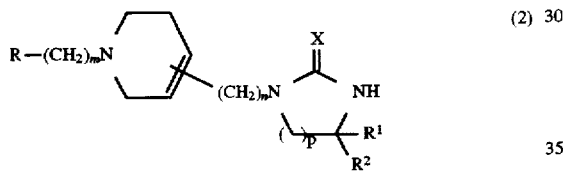

(2)

(wherein R, R$^1$, R$^2$, X, m, n and p are as described above), with compounds represented by a general formula (3)

(3)

(wherein Y denotes an eliminating group, and R$^4$ and q are as descried above), a general formula (4)

(4)

(wherein R$^4$, q and Y are as described above), or a general formula (5)

(5)

(wherein R$^5$ and Y are as described above), for 1 to 7 hours at 25° to 80° C. in a suitable solvent such as tetrahydrofuran, N,N-dimethylformamide, benzene or acetonitrile, using a suitable base such as sodium hydride or N,N-dimethylaminopyridine.

[B] The compounds represented by the general formula (1) or general formula (2) can be synthesized by reacting compounds represented by a general formula (6)

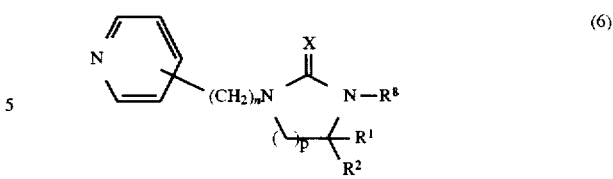

(6)

(wherein R$^8$ denotes a hydrogen atom or a formula

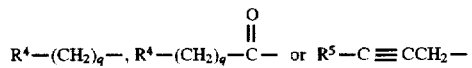

(wherein R$^4$, R$^5$ and q are as described above), and R$^1$, R$^2$, X, n and p are as described above), with compounds represented by a general formula (7)

(7)

(wherein R, Y and m are as descried as above), for 2 to 10 hours at 25° to 80° C. in a suitable solvent such as tetrahydrofuran, benzene or acetonitrile to synthesize compounds represented by a general formula (8)

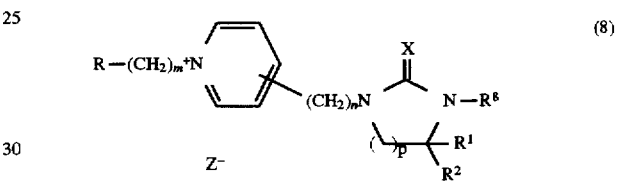

(8)

(wherein Z denotes a halogen atom, and R, R$^1$, R$^2$, R$^8$, X, m, n and p are as described above).

and by reacting these compounds represented by the general formula (8) for 2 to 10 hours at 0° to 20° C. in a suitable solvent such as methanol, ethanol or water or a mixture thereof in the presence of a reducing agent such as sodium borohydride.

The compounds represented by the general formula (6) are already known and can be synthesized according to Japan Patent Kokai No. Hei 2-49725, Chem. Pharm. Bull., 38(9), 2467 (1990), etc., but they can also be synthesized through following processed.

Compounds, R$^8$ being the formula

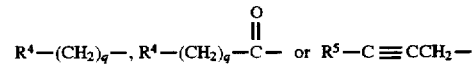

(wherein R$^4$, R$^5$ and n are as described above), among the compounds represented by the general formula (6), can be synthesized by reacting compounds represented by a general formula (6a)

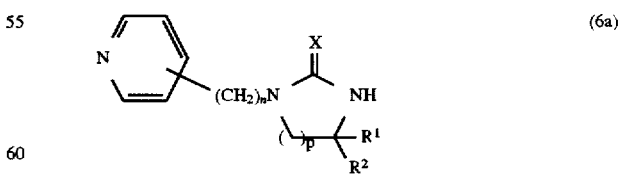

(6a)

(wherein R$^1$, R$^2$, X, n and p are as described above), with the compounds represented by the general formula (3)

(3)

(wherein R$^4$, q and Y are as described above), the general formula (4)

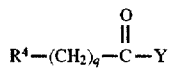
(4)

(wherein $R^4$, q and Y are as described above),
or the general formula (5)

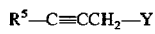
(5)

(wherein $R^5$ and Y are as described above),
according to the process [A].

Moreover, compounds, $R^8$ being

(wherein $R^4$ and q are as described above),
among the compounds represented by the general formula (6), can be synthesized by reacting compounds represented by a general formula (9)

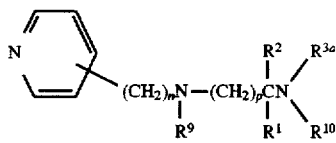
(9)

(wherin $R^{3a}$ denotes a formula

(wherein $R^4$ and q are as described above), either one or $R^9$ and $R^{10}$ denotes a hydrogen atom and the other denotes a formula

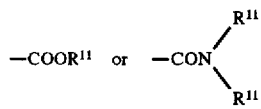

(wherein $R^{11}$ denotes identically or differently a hydrogen atom or lower alkyl group), and R, $R^1$, $R^2$, n and p are as described above),
for 1 to 3 hours at 150° to 250° C. in a suitable solvent such as toluene, diphenyl ether or N-methylpiperidone or with out solvent.

Furthermore, compounds, $R^8$ being

(wherein $R^4$ and q are as described above),
among the compounds represented by the general formula (6), can also be synthesized by reacting compounds represented by a general formula (10)

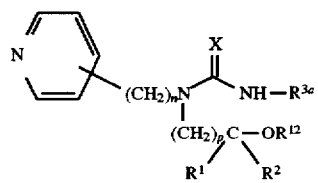
(10)

(wherein $R^{12}$ denotes a hydrogen atom, lower alkyl group or aralkyl group, and $R^1$, $R^2$, $R^{3a}$, n, p and X are as described above), for 2 to 5 hours at 90° to 150° C. in an acid such as hydrobromic acid or hydrochloric acid or in a halogenating agent such as thionyl chloride or phosphorus tribromide.

Here, the compounds represented by the general formula (9) can be synthesized according to, for example, following scheme.

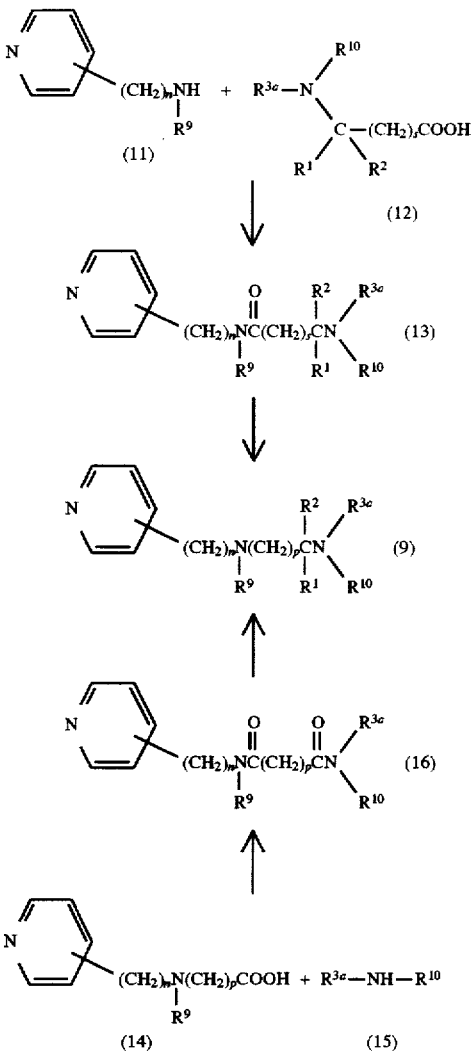

(wherein s denotes 0 to 2, and $R^1$, $R^2$, $R^{3a}$, $R^9$, $R^{10}$, n and p are as described above).

Namely, they can be synthesized in a way that corresponding amine derivatives and corresponding carboxylic acid derivatives, (11) and (12) or (14) and (15), are reacted for 2 to 5 hours at −10° to 20° C. in a suitable solvent such as tetrahydrofuran, N,N-dimethylformamide, benzene, dichloromethane or chloroform in the presence of a condensing agent such as N,N'-dicyclohexylcarbodiimide (DCC), phosphoryl cyanide (DEPC), 1-(3-dimethylaminopropyl)-3-ethylcarbodiimide hydrochloride (EDCI) or chloroformic ester to give amide form (13) or (16) and this is reacted for 2 to 6 hours at 0° C. to boiling point of solvent in a suitable solvent such as tetrahydrofuran, ether, dioxane or benzene in the presence of a reducing agent such as borane complex (borane-tetrahydofuran complex or borane-dimethyl sulfide complex).

Moreover, the compounds represented by the general formula (10) can be synthesized according to, for example, following scheme.

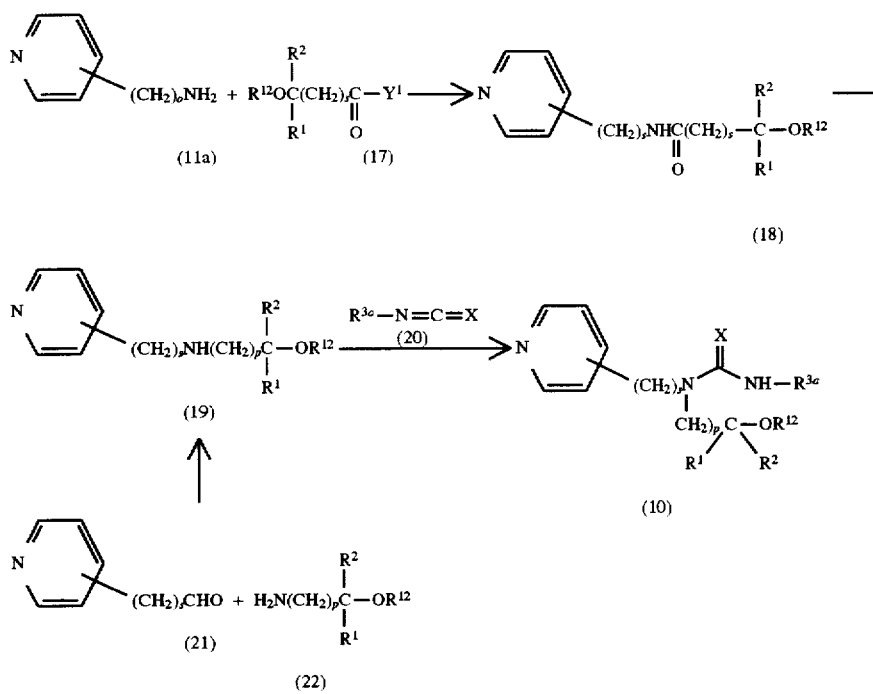

(wherein $Y^1$ denotes a hydroxyl group or halogen atom, and $R^1$, $R^2$, $R^{3a}$, $R^{12}$, X, n, s and p are as described above).

Namely, they can be synthesized in a way that corresponding amino form (11a) and corresponding carboxylic acid form or its acid halide (17) are reacted for 2 to 5 hours at 0° to 20° C. in a suitable solvent such as tetrahydrofuran, benzene, dichloromethane or chloroform in the presence of a condensing agent such as N,N'-dicyclohexylcarbodiimide (DCC) diethyl phosphoryl cyanide (DEPC) or 1-(3-dimethylaminopropyl)-3-ethylcarbodiimide•hydrochloride (EDCI) (acid anhydride process using chloroformic ester may also be used), or a suitable base such as triethylamine or pyridine to give amide form (18), this is reacted for 2 to 6 hour at 0° C. to boiling point of solvent in a suitable solvent such as tetrahydrofuran, ether, dioxane or benzene in the presence of a reducing agent such as borane complex (borane-tetrahydrofuran complex or borane-dimethyl sulfide complex) to convert to amine form (19), and then this is reacted with suitable isocyanic ester or isothiocyanic ester (20) for 2 to 6 hours at 0° to 150° C. in a suitable solvent such as tetrahydrofuran, benzene, dichloromethane, chloroform or N,N'-dimethylformamide or without solvent in the presence of a suitable base such as triethylamine or pyridine.

Here, the compounds of the general formula (19) can also be synthesized by reacting corresponding aldehyde form (21) and amino alcohol form (22) for 2 to 10 hours at 20° C. to boiling point of solvent in a suitable solvent such as toluene or xylene to the presence of a reducing agent such as sodium borohydride or sodium cyanoborohydride, or by catalytically reducing in an alcohol such as ethanol or methanol in the presence of a hydrogenation catalyst such as palladium carbon.

When pharmaceutically acceptable acid addition salts of the compounds represented by the general formula (1) are required, they can be obtained by reacting synthesized imidazolidinone derivatives with, for example, inorganic acids such as hydrochloric acid or organic acids such as maleic acid.

The preparative examples and the examples of the inventive compounds will be described to illustrate the invention in more detail.

Best embodiment for putting the invention into practice (EXAMPLE 1)

1-[3-(1-Phenylmethyl-1,2,5,6-tetrahydropyridyl)]-2-imidazolidinone

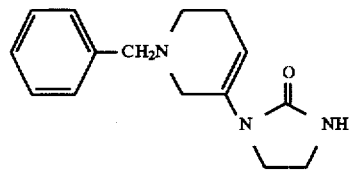

To a 70 ml acetonitrile solution of 5.00 g (30.6 mmol) of 1-(3-pyridyl)-2-imidazolidinone in a 100 ml round-bottomed flask were added 2.64 ml (1 eg.) of benzyl bromide at room temperature, and the mixture was refluxed for about 8 hours. After allowed to stand overnight, the crystals deposited were collected by filtration and washed with ethyl acetate to obtain solids.

These solids were suspended into 100 ml of ethanol and 2.32 g (2 eg.) of sodium borohydride were added by portions at 0° C. under stirring, which was then stirred for 4 hours at room temperature. After allowed to stand overnight, water was added to the reaction mixture and solvent was distilled off under reduced pressure. To the residue obtained were added 10 ml of saturated aqueous solution of sodium chloride, and the mixture was extracted 5 times with 30 ml of methylene chloride. The organic layers were combined, dried over anhydrous magnesium sulfate and then solvent was distilled off under reduced pressure. The residue thus obtained was recrystallized to obtain 2.53 g (yield 32%) of title compound.

mp. 120°–122° C. (acetonitrile) colorless powders

Elemental analysis (%); As $C_{15}H_{19}N_3$ O

Calculated: C: 70.01 H: 7.44 N: 16.33

Found; C: 69.72 H: 7.40 N: 16.42

(EXAMPLE 2)

1-[4-(1-Phenylmethyl-1,2,5,6-tetrahydropyridyl)]-2-imidazolidinone

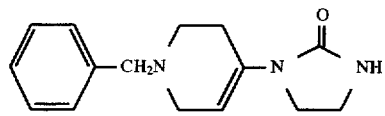

Using 1-(4-pyridyl)-2-imidazolidinone in place of 1-(3-pyridyl)-2-imidazolidinone, title compound was synthesized similarly to Example 1.

mp. 153°–154° C. (ethyl acetate) yellow plates

Elemental analysis (%); As $C_{15}H_{19}N_3O \cdot 0.1H_2O$

Calculated; C: 69.52 H: 7.47 N: 16.22

Found; C: 69.67 H: 7.23 N: 16.24

(EXAMPLE 3)

1-[4-(1-Phenylmethyl-1,2,5,6-tetrahydropyridyl)]-2(1H)-tetrahydropyrimidinone

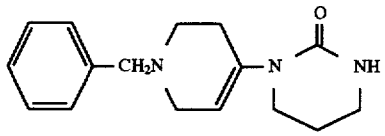

Using 1-(4-pyridyl)-2-(1H)-tetrahydropyrimidinone in place of 1-(3-pyridyl)-2-imidazolidinone, title compound was synthesized similarly to Example 1.

mp. 147°–148° C. (ethyl acetate) colorless needles

Elemental analysis (%); As $C_{16}H_{21}N_3$ O

Calculated; C: 70.82 H: 7.80 N: 15.48

Found; C: 70.54 H: 7.65 N: 15.55

(EXAMPLE 4)

1-[3-(1-Phenylmethyl-1,2,5,6-tetrahydropyridyl)]-3-(4-nitrophenyl)-2-imidazolidinone

To a 10 ml of distilled N,N-dimethylformamide solution of 0.30 g (1.17 mmol) of 1-[3-(1-phenylmethyl-1,2,5,6-tetrahydropyridyl)]-2-imidazolidinone (Example 1) placed in a 50 ml three-necked flask were added 46.6 mg (1 eg.) of sodium hydride at room temperature under stirring. After stirred for 30 minutes in an argon atmosphere, 124 µl (1 eg.) of 4-fluoronitrobenzene were added dropwise and the mixture was stirred for about 6 hours at room temperature.

The reaction mixture was poured into 10 ml of ice water. The crystals deposited were collected by filtration and rerystallized to obtain 260 mg (yield 58%) of title compound.

mp. 167°–168° C. (n-hexane-ethyl acetate) yellow plates

Elemental analysis (%); as $C_{21}H_{22}N_4$ $O_3 \cdot 0.2H_2O$

Calculated; C: 66.02 H: 5.91 N: 14.67

Found; C: 66.14 H: 5.78 N: 14.67

(EXAMPLES 5 through 12)

Using 1-[3-(1-phenylmethyl)-1,2,5,6-tetrahydropyridyl]-2-imidazolidinone (Example 1), 1-[4-(1-phenylmethyl)-1,2,5,6-tetrahydropyridyl]-2-imidazolidinone (Example 2) and 1-[4-(1-phenylmethyl)-1,2,5,6-tetrahydropyridyl]-2(1H)-tetrahydropyrimidinone (Example 3), following compounds were synthesized similarly to Example 4.

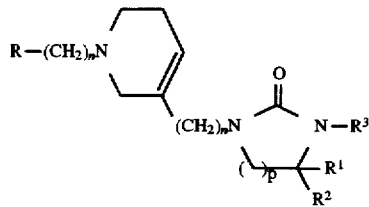

Examples 5–6

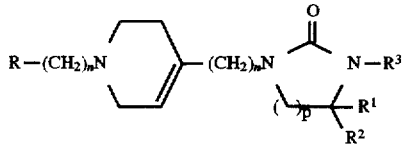

Examples 7–12

TABLE 1

| Example | R | R¹ R² | R³ | m | n | p | Melting point (Solvent for recrystallization) | Elemental analysis (%) calculated/Found |
|---|---|---|---|---|---|---|---|---|
| 5 | Ph | H | —CH₂—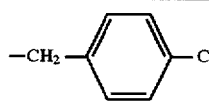—Cl | 1 | 0 | 1 | 92–94° C. (i-Pr₂O) | $C_{22}H_{24}ClN_3O$ C: 69.19 H: 6.33 N: 11.00 C: 69.14 H: 6.31 N: 10.99 |

TABLE 1-continued

| Example | R | R¹ R² | R³ | m | n | p | Melting point (Solvent for recrystallization) | Elemental analysis (%) calculated/Found |
|---|---|---|---|---|---|---|---|---|
| 6 | Ph | H | —(CH₂)₃CH₃ | 1 | 0 | 1 | 52–53° C. (n-hexane) | C₁₉H₂₇N₃O<br>C: 72.81 H: 8.68 N: 13.41<br>C: 72.80 H: 8.75 N: 13.22 |
| 7 | Ph | H | -C₆H₄-NO₂ (para) | 1 | 0 | 1 | 178–179° C. (n-Hexane: AcOEt) | C₂₁H₂₂N₄O₃<br>C: 66.65 H: 5.86 N: 14.81<br>C: 66.33 H: 5.82 N: 14.71 |
| 8 | Ph | H | —CH₂—C₆H₄—Cl | 1 | 0 | 1 | 154–155° C. (n-Hexane: AcOEt) | C₂₂H₂₄ClN₃O<br>C: 69.19 H: 6.33 N: 11.00<br>C: 69.14 H: 6.32 N: 10.98 |
| 9 | Ph | H | -C₆H₃(NO₂)(Cl) | 1 | 0 | 1 | 107–108° C. (n-Hexane: AcOEt) | C₂₁H₂₃ClN₄O₃<br>C: 61.09 H: 5.13 N: 13.57<br>C: 61.15 H: 5.08 N: 13.42 |

TABLE 2

| Example | R | R¹ R² | R³ | m | n | p | Melting point (Solvent for recrystallization) | Elemental analysis (%) calculated/Found |
|---|---|---|---|---|---|---|---|---|
| 10 | Ph | H | -C₆H₃(NO₂)(F) | 1 | 0 | 1 | 169–170° C. (n-Hexane: AcOEt) | C₂₁H₂₁FN₄O₃ · 0.2H₂O<br>C: 63.05 H: 5.29 N: 14.01<br>C: 63.29 H: 5.30 N: 14.01 |
| 11 | Ph | H | -C₆H₃(F)(NO₂) | 1 | 0 | 1 | 198–199° C. (n-Hexane: AcOEt) | C₂₁H₂₁FN₄O₃<br>C: 63.63 H: 5.34 N: 14.13<br>C: 63.44 H: 5.33 N: 13.98 |
| 12 | Ph | H | -C₆H₄-NO₂ | 1 | 0 | 2 | 126–127° C. (n-Hexane: AcOEt) | C₂₂H₂₄N₄O₃<br>C: 67.33 H: 6.16 N: 14.28<br>C: 67.02 H: 6.22 N: 14.18 |

(EXAMPLE 13)

1-[3-(1-Methyl-1,2,5,6-tetrahydropyridyl)]-3-(4-nitrophenyl)-2-imidazolidinone

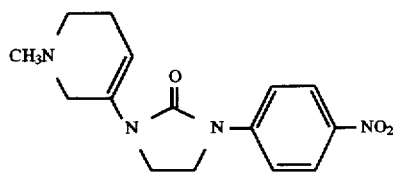

To a 60 ml acetonitrile solution of 1.00 g (3.52 mmol) of 1-(4-nitrophenyl)-3-(3-pyridyl)-2-imidazolidinone in a 50 ml sealed tube were added 0.22 ml (1 eg.) of methyl iodide, and the mixture was refluxed for 4 hours. After cooling, the reaction mixture was distilled off under reduced pressure and the residue obtained was washed with n-hexane by decantation to obtain 1.51 g of solids as needles.

mp. 281°–283° C.

This residue was taken into a 500 ml round-bottomed flask and dissolved by adding 100 ml of methanol, 15 ml of ethanol and 60 ml of water. After added 0.38 g (2 eg.) of sodium borohydride by portions at room temperature, the mixture was stirred for 1 hour at the same temperature. After allowed to stand overnight, the reaction mixture was stirred further for 7 hours and distilled off under reduced pressure to obtain the residue. To this residue were added 30 ml of saturated aqueous solution of sodium chloride, which was extracted 5 times with 40 ml of methylene chloride. The organic layers were combined, dried over anhydrous sodium sulfate, and solvent was distilled off under reduced pressure. The residue thus obtained was recrystallized to obtain 0.83 g (yield 78%) of title compound.

mp. 153°–155° C. (acetonitrile) yellow needles

Elemental analysis (%); As C₁₅H₁₈N₄O₃

Calculated; C: 59.59 H: 6.00 N: 18.53

Found C: 59.39 H: 5.92 N: 18.56

13

The starting material, 1-(4-nitrophenyl)-3-(3-pyridyl)-2-imidazolidinone was synthesized as follows:

(REFERENTIAL EXAMPLE 1)

1-(4-Nitrophenyl)-3-(3-pyridyl)-2-imidazolidinone

To a 300 ml dried N,N-dimethylformamide solution of 10.0 g (61.3 mmol) of 1-(3-pyridyl)-2-imidazolidinone in a 1 L three-necked flask were added gradually 2.45 g (1 eg.) of 60% sodium hydride at room temperature in an argon atmosphere, and then the mixture was stirred for 30 minutes at room temperature. To this reaction mixture were added dropwise 6.50 ml (1 eg.) of 4-fluoronitrobenzene, and, after stirred for 2 hours, the reaction mixture was poured into 3 L of ice water. Following stirring for same time, the crystals deposited were collected by filtration.

After air-dried the filtrated crystals, they were dried further at 100° C. under reduced pressure. These crystals were recrystallized to obtain 7.45 g (yield 43%) of 1-(4-nitrophenyl)-3-(3-pyridyl)-2-imidazolidinone.

mp. 229°–231° C. (acetonitrile) yellow needles

Elemental analysis (%); As $C_{14}H_{12}N_4 O_3$

Calculated; C: 59.15 H: 4.25 N: 19.72

Found; C: 59.31 H: 4.47 N: 19.56

(EXAMPLE 14)

1-[3-(1-Isopropyl-1,2,5,6-tetrahydropyridyl)]-3-(4-nitrophenyl)-2-imidazolidinone

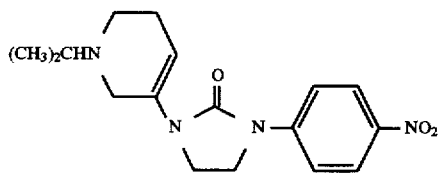

Using isopropyl iodide in place of methyl iodide, title compound was synthesized similarly to Example 13.

mp. 138°–140° C. (acetonitrile) yellow needles

Elemental analysis (%); As $C_{17}H_{22}N_4 O_3$

Calculated; C: 61.80 H: 6.71 N: 16.96

Found; C: 61.89 H: 6.76 N: 17.19

(EXAMPLE 15)

1-[3-(1-(4-Fluorophenylmethyl)-1,2,5,6-tetrahydropyridyl)]-3-(4-nitrophenyl)-2-imidazolidinone

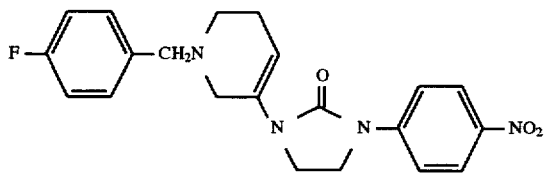

Using 4-fluorobenzyl chloride in place of methyl iodide, title compound was synthesized similarly to Example 13.

mp. 132°–134° C. (acetonitrile) orange plates

Elemental analysis (%); As $C_{21}H_{21}FN_4 O_3$

Calculated; C: 63.63 H: 5.34 N: 14.13

Found; C: 63.62 H: 5.41 N: 14.03

14

(EXAMPLE 16)

1-[3-(1-Phenylmethyl-1,2,5,6-tetrahydropyridyl)]-3-(4-acetylaminophenyl)-2-imidazolidinone

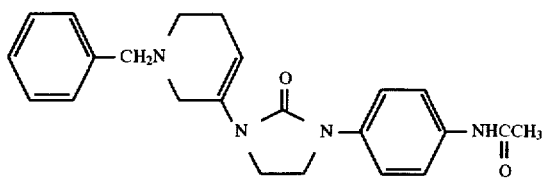

Using 1-(4-acetylaminophenyl)-3-(3-pyridyl)-2-imidazolidinone as a starting material and using benzyl bromide in place of methyl iodide, title compound was synthesized similarly to Example 13.

mp. 87°–89° C. (acetonitrile) light brown powders

Elemental analysis (%); As $C_{23}H_{26}N_4 O_2 \cdot 1.9H_2O$

Calculated; C: 65.04 H: 7.07 N: 13.19

Found; C: 65.14 H: 7.14 N: 12.98

The starting material, 1-(4-acetylaminophenyl)-3-(30 pyridyl)-2-imidazolidinone was synthesized as follows:

(REFERENTIAL EXAMPLE 2)

1-(4-Acetylaminophenyl)-3-(3-pyridyl)-2-imidazolidinone (A); 1-(4-aminophenyl)-3-(3-pyridyl)-2-imidazolidinone To 1.96 g (5 eg.) of iron powder in a 50 ml round-bottomed flask were added 18 ml of acetic acid, and, after stirred for 20 minutes, 2.00 g (7.04 mmol) of 1-(4-nitrophenyl)-3-(3-pyridyl)-2-imidazolidinone were added. The reaction mixture was stirred for 4 hours at 60° C. and then was distilled off under reduced pressure.

Water was added to the residue and iron powder was collected by filtration to remove. The filtrate was made to be pH of 12 or higher by using aqueous solution of potassium hydroxide, which was extracted 8 times with 10 ml of methylene chloride. The organic layers were combined, dried over anhydrous sodium sulfate, and then solvent was distilled off under reduced pressure to obtain 0.57 g (yield 32%) of 1-(4-aminophenyl)-3-(3-pyridyl)-2-imidazolidinone as light brown powders $^1$H-NMR (TMS in $d_6$-DMSO, 90 MHz)

δ 3.91 (4H, bs), 4.96 (2H, bs), 6.57 (2H, d, J=9.0 Hz), 7.22 (2H, d, J=9.0 Hz), 7.33–7.55 (1H, m), 7.95–8.08 (1H, m), 8.17 (1H, dd, J=4.4, 3.1 Hz), 8.81 (1H, d, J=2.0 Hz)

(B); 1-(4-Acetylaminophenyl)-3-(3-pyridyl)-2-imidazolidinone

To a 10 ml dried methylene chloride solution of 0.57 g (2.24 mmol) of 1-(4-aminophenyl)-3-(3-pyridyl)-2-imidazolidinone in a 100 ml round-bottomed flask were added 0.34 ml (1.1 eg.) of triethylamine, and, after stirred for 15 minutes, 0.17 ml (1.1 eg.) of acetyl chloride were added dropwise under cooling with ice. After dropwise addition, the mixture was stirred for 8 hours at room temperature. To this reaction mixture were added 10 ml of saturated aqueous solution of sodium chloride, and the organic layer was separated. The organic layer was dried over anhydrous sodium sulfate and then solvent was distilled off under reduced pressure to obtain 0.16 g (yield 24%) of 1-(4-acetylaminophenyl)-3-(3-pyridyl)-2-imidazolidinone.

$^1$H-NMR (TMS in $d_6$-DMSO, 90 MHz)

δ 2.04 (3H, s), 3.28–3.52 (4H, m), 7.12–7.68 (5H, m), 7.92–8.08 (1H, m), 8.12–8.24 (1H, m), 8.76 (1H, bs), 9.92 (1H, bs)

(EXAMPLE 17)

1-[3-(1-Phenylmethyl-1,2,5,6-tetrahydropyridyl)]-3-(4-chlorophenyl)-2-imidazolidinone

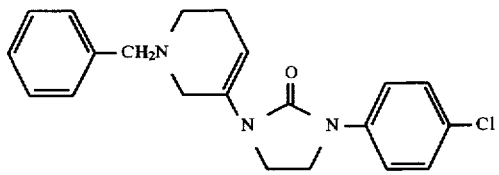

(A); 1-(4-Chlorophenyl)-3-(3-pyridyl)-2-imidazolidinone

A 10 ml toluene solution of 4.54 g (14.8 mmol) of N-(4-chlorophenyl)-N-methoxycarbonyl-N'-(3-pyridyl)ethylenediamine in a 100 ml round-bottomed flask was heated gradually and, while distilling off toluene, it was heated for 1.5 hours at 190° to 210° C. The amorphous reaction mixture was cooled to room temperature and methylene chloride was added to dissolve. This was purified by column chromatography (silica gel, ethyl acetate:n-hexane=5:1) to obtain 2.28 g (yield 56%) of 1-(4-chlorophenyl)-3-(3-pyridyl)-2-imidazolidinone as brown crystals.

Mass; $C_{14}H_{12}ClN_3$ O m/e: 273 ($M^+$ base), 139, 125, 111, 92, 78

(B); 1-[3-(1-Phenylmethyl-1,2,5,6-tetrahydropyridyl)]-3-(4-chlorophenyl)-2-imidazolidinone To a 30 ml acetonitrile solution of 1.10 g (4.02 mmol) of 1-(4-chlorophenyl)-3-(3-pyridyl)-2-imidazolidinone in a 100 ml round-bottomed flask were added 0.48 ml (1 eg.) of benzyl bromide, and the mixture was refluxed for 2 hours. After cooling, the reaction mixture was distilled off under reduced pressure and the residue obtained was washed thrice with 20 ml of n-hexane by decantation to obtain solids. These solids were dissolved by adding 200 ml of methanol and 70 ml of water, 0.30 g (2 eg.) of sodium borohydride were added by portions at room temperature, and then the mixture was reacted for 3.5 hours at the same temperature under stirring. After allowed to stand overnight, the reaction mixture was concentrated under reduced pressure and water was added, which was extracted thrice with 100 ml of methylene chloride. The organic layers were combined and, after dried over anhydrous magnesium sulfate, the residue obtained by distilling off solvent under reduced pressure was purified by column chromatography (silica gel, ethyl acetate) and recrystallized to obtain 0.63 g (yield 43%) of title compound.

mp. 123°–124° C. (2-propanol) colorless needles

Elemental analysis (%); As $C_{21}H_{22}ClN_3$ O

Calculated; C: 68.56 H: 6.03 N: 11.42

Found; C: 68.49 H: 6.09 N: 11.46

The starting raw material, N-(4-chlorophenyl)-N-methoxycarbonyl-N'-(3-pyridyl)ethylenediamine was synthesized as follows:

(REFERENTIAL EXAMPLE 3)

N-(4-Chlorophenyl)-N-methoxycarbonyl-N'-(3-pyridyl)-ethylenediamine (A); 2-[N-(4-chlorophenyl)-N-methoxycarbonyl]amino-N'-(3-pyridyl)acetamide To a 15 ml distilled methylene chloride solution of 1.25 g (1.01 eg.) of N-methoxycarbonyl-N-4-chlorophenylglycine in a 100 ml round-bottomed flask were added 1.08 g (1.10 eg.) of EDCI [1-(3-dimethylaminopropyl)-3-ethylcarbodiimide·hydrochloride] by portions at room temperature. Thereafter, 0.48 g (5.10 mmol) of 3-aminopyridine were added further by portions. This reaction mixture was stirred for 4 hours at room temperature and after allowed to stand overnight, water was added and the organic layer was separated. The aqueous layer was extracted twice with 30 ml of methylene chloride. These were combined with previously separated organic layer and, after dried over anhydrous sodium sulfate, solvent was distilled off under reduced pressure to obtain the residue. This was purified by column chromatography (alumina, ethyl acetate:n-hexane=5:2, later methylene chloride:methanol=20:1) to obtain 1.03 g (yield 63%) of 2-[N-(4-chlorophenyl)-N-methoxy carbonyl]amino-N'-(3-pyridyl)acetamide as a brown oil.

Mass; $C_{15}H_{14}ClN_3$ $O_3$ m/e: 319 ($M^+$), 287, 198, 139, 78 (base)

(B); N-(4-chlorophenyl)-N-methoxycarbonyl-N'-(3-pyridyl)ethylenediamine

To a 14.5 ml solution (4.5 eg.) of 1M borane·tetrahydrofuran complex in a 100 ml round-bottomed flask was added slowly dropwise a 20 ml distilled tetrahydrofuran solution of 1.08 g (3.22 mmol) of 2-[N-(4-chlorophenyl)-N-methoxycarbonyl]-amino-N'-(3-pyridyl)acetamide in an argon atmosphere under cooling with ice. Thereafter, the mixture was stirred for 30 minutes at room temperature and further refluxed for 2 hours. The reaction mixture was cooled to room temperature and it was added carefully to 40 ml of 6N hydrochloric acid in a 300 ml round-bottomed flask at room temperature, which was then refluxed for 2.5 hours. The reaction mixture was concentrated under reduced pressure and water was added. After washed with ethyl acetate and separated the aqueous layer, the organic layer was extracted again with 1N hydrochloric acid (50 ml). This was combined with previous aqueous layer and, while cooling with ice, pH was made 12 or higher with potassium hydroxide. The alkaline aqueous layer was extracted thrice with 200 ml of ethyl acetate and further twice with 100 ml of methylene chloride. The organic layers were combined and, after dried over anhydrous magnesium sulfate, the residue obtained by distilling off solvent under reduced pressure was purified by column chromatography (alumina, ethyl acetate:n-hexane=1:1) to obtain 0.84 g (yield 85%) of N-(4-chlorophenyl)-N-methoxycarbonyl-N'-(3-pyridyl)ethylenediamine as a light brown oil.

Mass; $C_{15}H_{16}ClN_3$ $O_2$ m/e: 305 ($M^+$), 193, 107 (base)

(EXAMPLE 18)

1-[3-(1-Methyl-1,2,5,6-tetrahydropyridyl)]-3-(4-chlorophenyl)-2-imidazolidinone

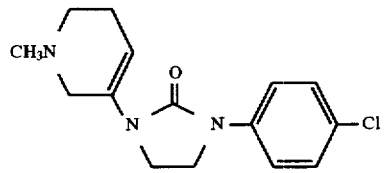

Using methyl iodide in place of benzyl bromide, title compound was synthesized by the similar method to Example 17-(B).

mp. 117°–118° C. (acetonitrile) colorless prisms

Elemental analysis (%); As $C_{15}H_{19}N_3$ O

Calculated; C: 61.75 H: 6.22 N: 14.40

Found; C: 61.65 H: 6.38 N: 14.44

(EXAMPLE 19)

1-[3-(1-Phenylmethyl-1,2,5,6-tetrahydropyridylmethyl)]-3-(4-chlorophenyl)-2-imidazolidinone•hydrochloride

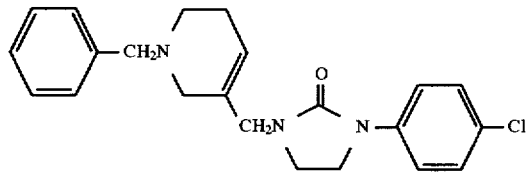

(A); 1-(4-chlorophenyl)-3-(3-pyridylmethyl)-2-imidazolidinone

To 5.81 g (14.7 mmol) of N-(4-chlorophenyl)-N'-(3-pyridylmethyl)-N'-2-(benzyloxy)ethyl urea in a 100 ml round-bottomed flask were added 65 ml of 48% hydrobromic acid at room temperature. The mixture was heated gradually and then heated for 4 hours at 95° to 100° C. The reaction mixture was cooled to room temperature. 20 ml of water were added, and further 50 ml of ethyl acetate were added to extract. The ethyl acetate layer was extracted with 30 ml of 6N hydrochloric acid, which was combined with previous aqueous layer. While cooling this with ice, pH was made to be 12 or higher with potassium hydroxide and extracted thrice with 100 ml of methylene chloride. The organic layers were combined, dried over anhydrous sodium sulfate, and then solvent was distilled off under reduced pressure to obtain 2.28 g (yield 54%) of 1-(4-chlorophenyl)-3-(3-pyridylmethyl)-2-imidazolidinone as brown crystals.

1H-NMR (TMS in $CDCl_3$, 90 MHz)

δ 3.28–3.47 (2H, m), 3.71–3.89 (2H, m), 4.48 (2H, m), 7.22–7.75 (8H, m), 8.52–8.57 (2H, m)

(B); 1-[3-(1-Phenylmethyl-1,2,5,6-tetrahydropyridylmethyl)]-3-(4-chlorophenyl)-2-imidazolidinone•hydrochloride Using 1-(4-chlorophenyl)-3-(3-pyridylmethyl)-2-imidazolidinone, 1-[3-(1-phenylmethyl-1,2,5,6-tetrahydropyridylmethyl)]-3-(4-chlorophenyl)-2-imidazolidinone was obtained as a brown oily product by the similar method to Example 17-(B). This residue was treated with saturated ether-hydrochloric acid in ethyl acetate and recrystallized to obtained as a brown oil by the similar method to Example 17-(B). This residue was treated with saturated ether-hydrochloric acid in ethyl acetate and recrystallized to obtain 0.18 g (yield 17%) of title compound.

mp. 235°–237° C. (ethanol) light brown prisms

Elemental analysis (%); As $C_{22}H_{24}ClN_3$ O HCl

Calculated; C: 63.16 H: 6.02 N: 10.04

Found; C: 63.04 H: 6.09 N: 9.84

The starting raw material, N-(4-chlorophenyl)-N'-(3-pyridylmethyl)-N'-[2-(benzyloxy)ethyl]urea was synthesized as follows:

(REFERENTIAL EXAMPLE 4)

N-(4-chlorophenyl)-N'-(3-pyridylmethyl)-N'-[2-(benzyloxy)ethyl]urea (A); 3-[N-2-(benzyloxy)ethyl]pyridylmethanamine To a 70 ml methanol solution of 3.50 g (32.7 mmol) of pyridine-3-aldehyde in a 200 ml round-bottomed flask were added 4.94 g (1 eg.) of O-benzylethanolamine at room temperature, and the mixture was stirred for 2 hours at the same temperature. Then, 2.47 g (2 eg.) of sodium borohydride were added gradually and the mixture was stirred further for 5 hours at room temperature, which was allowed to stand overnight. The reaction mixture was distilled off under reduced pressure and water was added to the residue, which was extracted thrice with 200 ml of methylene chloride. The organic layers were dried over anhydrous sodium sulfate and then solvent was distilled off under reduced pressure to obtain 7.59 g (yield 96%) of 3-[N-2-(benzyloxy)ethyl]-pyridylmethaneamine as a pale yellow oil. This was used for next reaction as it is without purification.

(B); N-(4-chlorophenyl)-N'-(3-pyridylmethyl)-N'[2-(benzyloxy)ethyl]urea

To a 30 ml tetrahydrofuran solution of 2.35 g (9.70 mmol) of 3-[N-2-(benzyloxy)ethyl]pyridylmethaneamine in a 100 ml round-bottomed flask were added dropwise 1.24 ml (1 eg.) of 4-chlorophenyl isocyanate at room temperature, and the reaction mixture was stirred for 8 hours at room temperature. After allowed to stand overnight, solvent was distilled off under reduced pressure and water was added to the residue obtained. This was made to be pH of 12 or higher with potassium hydroxide and extracted thrice with 100 ml of methylene chloride. The organic layers were combined, dried over anhydrous sodium sulfate and then solvent was distilled off under reduced pressure to obtain the residue. This was purified by column chromatography (silica gel, n-hexane:ethyl acetate=2:1) to obtain 2.93 g (yield 76%) of N-(4-chlorophenyl)-N'-(3-pyridylmethyl)-N'-[2-(benzyloxy)ethyl]-urea as a dark brown oil.

Mass; $C_{22}H_{22}ClN_3$ $O_2$ m/e: 395 (M$^+$), 304, 153, 121 (base)

(EXAMPLE 20)

1-[3-(1-Phenylmethyl-1,2,5,6-tetrahydropyridyl)]-3-(4-nitrophenyl)-2-imidazolidinone•maleate To a 5 ml methanol solution of 0.20 g of 1-[3-(1-phenylmethyl-1,2,5,6-tetrahydropyridyl)]-3-(4-nitrophenyl)-2-imidazolidinone synthesized in Example 4 were added 61.5 mg of maleic acid under heat, and the mixture was heated further for 10 minutes. The reaction mixture was cooled to room temperature and, after collected the crystals deposited by filtration, they were recrystallized to obtain 0.17 g (yield 65%) of title compound.

mp. 168°–169° C. (methanol-water) pale yellow powder

Elemental analysis (%); As $C_{21}H_{22}N_4$ $O_3 \cdot C_4H_4O_4$

Calculated; C: 60.72 H: 5.30 N: 11.33

Found; C: 60.52 H: 5.26 N: 11.36

(EXAMPLE 21)

1-[3-(1-Phenylmethyl-1,2,5,6-tetrahydropyridyl)]-3-(4-chlorophenyl)-2-imidazolidinone•maleate Using 1-[3-(1-phenylmethyl-1,2,5,6-tetrahydropyridyl)]-3-(4-chlorophenyl)-2-imidazolidinone synthesized in Example 17, title compound was synthesized similarly to Example 20.

mp. 154°–155° C. (methanol) colorless primsms

Elemental analysis (%); As $C_{21}H_{22}$ $ClN_3$ $O \cdot C_4$ $H_4$ $O_4 \cdot 0.2H_2O$ Calculated; C: 61.59 H: 5.46 N: 8.62

Found; C: 61.65 H: 5.34 N: 8.68

(EXAMPLE 22)

1-[3-(1-Phenylmethyl)-1,2,5,6-tetrahydropyridyl]-3-(4-chlorophenyl)-2-imidazolidinone·phosphate To a 170 ml acetonitrile solution of 3.00 g (8.15 mmol) of 1-[3-(1-phenylmethyl)-1,2,5,6-tetahydropyridyl]-3-(4-chlorophenyl)-2-imidazolidinone (Example 17) was added dropwise a 5 ml acetonitrile solution of 0.95 g (1.0 eg.) of 85% phosphoric acid at room temperature under stirring, and the mixture was stirred for 1 hour at room temperature. The deposits obtained were collected by filtration, suspended into 100 ml of ethanol, and the suspension was stirred for 30 minutes at room temperature. The crystals were collected by filtration and dried to obtain 3.43 g (yield 90%) of title compound.

mp. 145°–147° C. light brown powders

Elemental analysis (%); As $C_{21}H_{22}ClN_3 O \cdot H_3 PO_4$

Calculated; C: 54.14 H: 5.41 N: 9.02

Found; C: 54.12 H: 5.39 N: 9.13

(EXAMPLES 23 through 43)

Using 1-(4-chlorophenyl)-3-(3-pyridyl)-2-imidazolidinone (Example 17-A) as a starting material and using corresponding aralkyl halides, following compounds were synthesized similarly to Example 17-B.

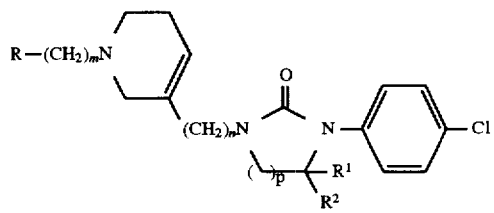

TABLE 3

| Example | R | R¹ R² | m | n | p | Melting point (Solvent for recrystallization) | Elemental analysis (%) Calculated/Found |
|---|---|---|---|---|---|---|---|
| 23 | Br—C₆H₄— | H | 1 | 0 | 1 | 136–137° C. (CH₃CN) | $C_{21}H_{21}BrClN_3 O$<br>C: 56.46 H: 4.74 N: 9.41<br>C: 56.66 H: 4.60 N: 9.46 |
| 24 | NC—C₆H₄— | H | 1 | 0 | 1 | 170–171° C. (CH₃CN) | $C_{22}H_{21}ClN_4 O$<br>C: 67.26 H: 5.39 N: 14.26<br>C: 67.16 H: 5.47 N: 14.50 |
| 25 | EtO—C₆H₄— | H | 1 | 0 | 1 | 173–174° C. (CH₃CN) | $C_{23}H_{26}ClN_3 O_2$<br>C: 67.06 H: 6.36 N: 10.20<br>C: 67.12 H: 6.26 N: 10.36 |
| 26 | iPr—C₆H₄— | H | 1 | 0 | 1 | 153–154° C. (CH₃CN) | $C_{24}H_{28}ClN_3 O$<br>C: 70.32 H: 6.88 N: 10.25<br>C: 70.11 H: 6.84 N: 10.30 |
| 27 | 2-naphthyl | H | 1 | 0 | 1 | 142–143° C. (CH₃CN) | $C_{25}H_{24}ClN_3 O$<br>C: 71.85 H: 5.79 N: 10.05<br>C: 71.93 H: 5.81 N: 10.16 |
| 28 | phenyl | H | 3 | 0 | 1 | 104–105° C. (CH₃CN) | $C_{23}H_{26}ClN_3 O$<br>C: 69.77 H: 6.62 N: 10.61<br>C: 70.01 H: 6.61 N: 10.65 |
| 29 | F₃C—C₆H₄— | H | 1 | 0 | 1 | 159–160° C. (CH₃CN) | $C_{22}H_{21}ClF_3 N_3 O$<br>C: 60.62 H: 4.86 N: 9.64<br>C: 60.80 H: 4.92 N: 9.70 |

TABLE 4

| Example | R | R¹ R² | m | n | p | Melting point (Solvent for recrystallization) | Elemental analysis (%) Calculated/Found |
|---|---|---|---|---|---|---|---|
| 30 | Me—C₆H₄— | H | 1 | 0 | 1 | 159–160° C. (CH₃CN) | $C_{22}H_{24}ClN_3 O$<br>C: 69.19 H: 6.33 N: 11.00<br>C: 69.18 H: 6.33 N: 11.11 |

TABLE 4-continued

| Example | R | R¹ R² | m | n | p | Melting point (Solvent for recrystallization) | Elemental analysis (%) Calculated/Found |
|---|---|---|---|---|---|---|---|
| 31 | 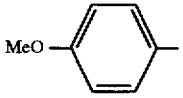 MeO— | H | 1 | 0 | 1 | 153–154° C. (CH₃CN) | $C_{22}H_{24}ClN_3O_2$<br>C: 66.41 H: 6.08 N: 10.56<br>C: 66.32 H: 6.10 N: 10.67 |
| 32 | 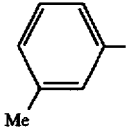 Me | H | 1 | 0 | 1 | 135–136° C. (CH₃CN) | $C_{22}H_{24}ClN_3O$<br>C: 69.19 H: 6.33 N: 11.00<br>C: 69.15 H: 6.43 N: 11.16 |
| 33 | 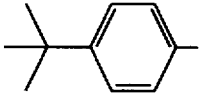 | H | 1 | 0 | 1 | 180–181° C. (CH₃CN) | $C_{25}H_{30}ClN_3O$<br>C: 70.82 H: 7.13 N: 9.91<br>C: 70.83 H: 7.23 N: 9.94 |
| 34 | 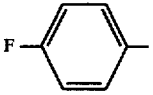 F— | H | 1 | 0 | 1 | 130–132° C. (CH₃CN) | $C_{21}H_{21}ClFN_3O$<br>C: 65.37 H: 5.49 N: 10.89<br>C: 65.31 H: 5.57 N: 10.88 |
| 35 | 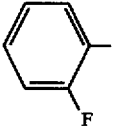 F | H | 1 | 0 | 1 | 115–118° C. (CH₃CN) | $C_{21}H_{21}ClFN_3O$<br>C: 65.37 H: 5.49 N: 10.89<br>C: 65.47 H: 5.55 N: 10.85 |
| 36 | 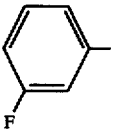 F | H | 1 | 0 | 1 | 111–114° C. (cyclohexane) | $C_{21}H_{21}ClFN_3O$<br>C: 65.37 H: 5.49 N: 10.89<br>C: 65.10 H: 5.37 N: 10.83 |

TABLE 5

| Example | R | R¹ R² | m | n | p | Melting point (Solvent for recrystallization) | Elemental analysis (%) Calculated/Found |
|---|---|---|---|---|---|---|---|
| 37 | 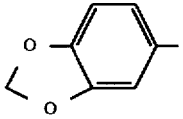 | H | 1 | 0 | 1 | 173–175° C. (CH₃CN) | $C_{22}H_{22}ClN_3O_3$<br>C: 64.15 H: 5.38 N: 10.20<br>C: 64.14 H: 5.42 N: 10.41 |
| 38 | 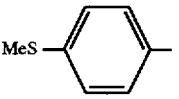 MeS— | H | 1 | 0 | 1 | 128–131° C. (CH₃CN) | $C_{22}H_{24}ClN_3OS$<br>C: 63.83 H: 5.84 N: 10.15<br>C: 63.62 H: 5.92 N: 10.16 |
| 39 | 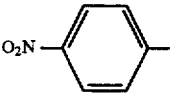 O₂N— | H | 1 | 0 | 1 | 138–141° C. (2-Propanol) | $C_{21}H_{21}ClN_4O_3$<br>C: 61.09 H: 5.13 N: 13.57<br>C: 60.97 H: 5.03 N: 13.50 |
| 40 | 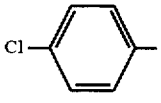 Cl— | H | 1 | 0 | 1 | 117–119° C. (CH₃CN) | $C_{21}H_{21}Cl_2N_3O$<br>C: 62.69 H: 5.26 N: 10.44<br>C: 62.46 H: 5.13 N: 10.47 |
| 41 | 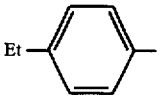 Et— | H | 1 | 0 | 1 | 127–129° C. (CH₃CN) | $C_{23}H_{26}ClN_3O$<br>C: 69.77 H: 6.62 N: 10.61<br>C: 69.86 H: 6.62 N: 10.62 |

TABLE 5-continued

| Example | R | R¹ R² | m | n | p | Melting point (Solvent for recrystallization) | Elemental analysis (%) Calculated/Found |
|---|---|---|---|---|---|---|---|
| 42 | biphenyl | H | 1 | 0 | 1 | 195–197° C. (CH$_2$Cl$_2$) | C$_{27}$H$_{26}$ClN$_3$O<br>C: 73.04 H: 5.90 N: 9.46<br>C: 72.90 H: 5.92 N: 9.46 |
| 43 | cyclohexyl (H) | H | 1 | 0 | 1 | 150–151° C. (CH$_3$CN) | C$_{21}$H$_{28}$ClN$_3$O<br>C: 67.45 H: 7.55 N: 11.24<br>C: 67.73 H: 7.49 N: 11.17 |

(EXAMPLES 44 through 48)

Using corresponding halides etc. in place of 4-fluoronitrobenzene and using 1-[3-(1-phenylmethyl)-1,2,3,6-tetrahydropyridyl]-2-imidazolidinone (Example 1) as a starting material, following compounds were synthesized similarly to Example 4.

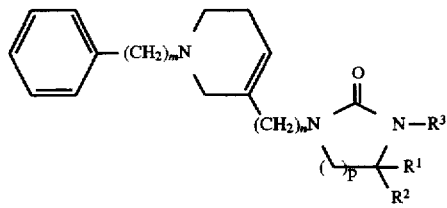

(EXAMPLE 49)

1-[3-(1-Phenylmethyl)-1,2,5,6-tetrahydropyridyl]-3-(3-pyridylmethyl)-2-imidazolidinone

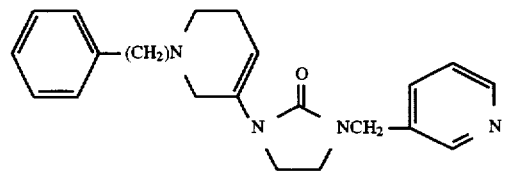

Using 3-chloromethylpyridine-hydrochloride in place of 4-fluoronitrobenzene, title compound was synthesized similarly to Example 4. Brown oil.

$^1$H-NMR (TMS in CDCl$_3$, 400 MHz)

δ 2.23 (2H, brs), 2.53 (2H, t, J=5.9 Hz), 3.24 (1H, d, J=9.8 Hz), 3.26 (1H, d, J=8.8 Hz), 3.50 (1H, d, J=8.8 Hz), 3.52 (1H, d, J=9.8 Hz), 3.67 (2H, s), 3.68 (2H, s), 4.37 (2H, s),

TABLE 6

| Example | R¹ | R¹ R² | m | n | p | Melting point (Solvent for recrystallization) | Elemental analysis (%) Calculated/Found |
|---|---|---|---|---|---|---|---|
| 44 | NC–C$_6$H$_4$– | H | 1 | 0 | 1 | 146–149° C. (CH$_3$CH) | C$_{22}$H$_{22}$N$_4$O<br>C: 73.72 H: 6.19 N: 15.63<br>C: 73.55 H: 6.23 N: 15.64 |
| 45 | Cl–C$_6$H$_4$–C(O)– | H | 1 | 0 | 1 | 205–207° C. (CH$_3$CH) | C$_{22}$H$_{22}$ClN$_3$O$_2$<br>C: 66.75 H: 5.60 N: 10.61<br>C: 66.65 H: 5.60 N: 10.61 |
| 46 | Cl–C$_6$H$_4$–CH$_2$–C(O)– | H | 1 | 0 | 1 | 94–96° C. (2-Propanol) | C$_{23}$H$_{24}$ClN$_3$O$_2$<br>C: 67.39 H: 5.90 N: 10.25<br>C: 67.15 H: 5.85 N: 10.24 |
| 47 | cyclohexyl-CH$_2$– | H | 1 | 0 | 1 | 93–95° C. (n-Hexane) | C$_{22}$H$_{31}$N$_3$O<br>C: 74.75 H: 8.84 N: 11.89<br>C: 74.56 H: 8.90 N: 11.77 |
| 48 | 2-naphthyl-CH$_2$– | H | 1 | 0 | 1 | 104–107° C. (CH$_3$CH) | C$_{26}$H$_{27}$N$_3$O<br>C: 78.56 H: 6.85 N: 10.57<br>C: 78.46 H: 6.91 N: 10.73 |

4.97 (1H, brs), 7.27–7.39 (6H, m), 6.63 (1H, d, J=7.8 Hz), 8.51–8.55 (2H, m)

H. R. Mass; As $C_{21}H_{24}N_4$ O

Calculated; m/Z: 348.1950, Found; m/z: 348.1919

(EXAMPLE 50)

1-[3-(1-Phenylmethyl)-1,2,5,6-tetrahydropyridyl]-3-(2-chlorophenyl)-2-imidazolidinone

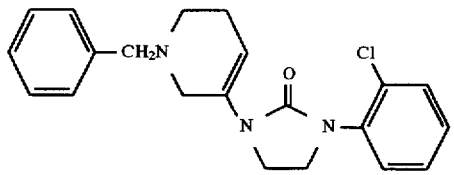

A 70 ml acetonitrile solution of 5.00 g (18.3 mmol) of 1-(2-chlorophenyl)-3-(3-pyridyl)-2-imidazolidinone in a 300 ml round-bottomed flask were added 2.18 ml (1 eg.) of benzyl bromide, and the mixture was refluxed for 4 hours. After cooling, the reaction mixture was distilled off under reduced pressure and the residue obtained was washed thrice with 50 ml of n-hexane by decantation. The solids obtained were dissolved by adding 200 ml of methanol, 1.39 g (2 eg.) of sodium borohydride were added by portions under stirring and cooling with ice, and then the mixture was reacted for 2 hours at room temperature under stirring. After allowed to stand overnight, 0.70 g (1 eg.) of sodium borohydride were added further and the mixture was stirred for 1 hour at room temperature. Then, the reaction mixture was distilled off under reduced pressure and water was added to the residue obtained, which was extracted 4 times with 50 ml of methylene chloride. The organic layers were combined, dried over anhydrous sodium sulfate, and then solvent was distilled off under reduced pressure. The residue thus obtained was purified by column chromatography (silica gel, ethyl acetate) and recrystallized to obtain 4.43 g (yield 66%) of title compound.

mp. 98°–101° C. (cyclohexane) light brown powders

Elemental analysis (%); As $C_{21}H_{22}ClN_3$ O

Calculated; C: 68.56 H: 6.03 N: 11.42

Found; C: 68.46 H: 6.03 N: 11.40

The starting material, 1-(2-chlorophenyl)-3-(3-pyridyl)-2-imidazolidinone was synthesized from N-methoxycarbonyl-N-2-chlorophenylglycine similarly to Referential example 3 (A) and (B) and Example 17-A.

(EXAMPLE 51)

1-[3-(1-Phenylmethyl)-1,2,5,6-tetrahydropyridyl]-3-(3-chlorophenyl)-2-imidazolidinone

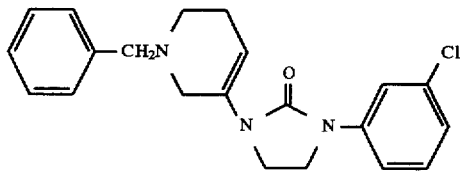

Using 1-(3-chlorophenyl)-3-(3-pyridyl)-2-imidazolidinone in place of 1-(2-chlorophenyl)-3-(3-pyridyl)-2-imidazolidinone as a starting material, title compound was synthesized similarly to Example 50.

mp. 110°–112° C. (2-propanol) pale yellow powders

Elemental analysis (%); As $C_{21}H_{22}ClN_3$ O

Calculated; C: 68.56 H: 6.03 N: 11.42

Found; C: 68.67 H: 6.11 N: 11.45

The starting material, 1-(3-chlorophenyl)-3-(3-pyridyl)-2-imidazolidinone was synthesized from N-methoxycarbonyl-N-3-chlorophenylglycine similarly to Referential example 3 (A) and (B) and Example 17-A.

(EXAMPLE 52)

1-[3-(1-Phenylmethyl)-1,2,5,6-tetahydropyridyl]-3-(4-fluorophenyl)-2-imidazolidinone

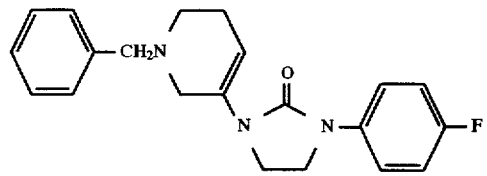

Using 1-(4-fluorophenyl)-3-(3-pyridyl)-2-imidazolidinone in place of 1-(2-chlorophenyl)-3-(3-pyridyl)-2-imidazolidinone as a starting material, title compound was synthesized similarly to Example 50.

mp. 97°–98° C. (diisopropylether) pale yellow prisms

Elemental analysis (%); As $C_{21}H_{22}$ $FN_3$ O

Calculated; C: 71.77 H: 6.31 N: 11.96

Found; C: 71.93 H: 6.49 N: 11.89

The starting material, 1-(4-fluorophenyl)-3-(3-pyridyl)-2-imidazolidinone was synthesized from N-methoxycarbonyl-N-4-fluorophenylglycine similarly to Referential example 3 (A) and (B) and Example 17-A.

(EXAMPLE 53)

1-[3-(1-Phenylmethyl)-1,2,5,6-tetrahydropyridyl]-3-(4-trifluoromethylphenyl)-2-imidazolidinone

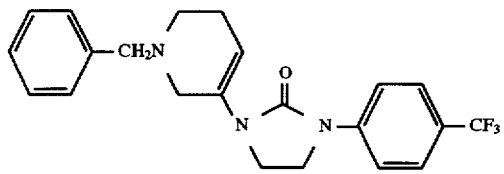

Using 1-(4-trifluoromethylphenyl)-3-(3-pyridyl)-2-imidazolidinone as a starting material in place of 1-(2-chlorophenyl)-3-(3-pyridyl)-2-imidazolidinone, title compound was synthesized similarly to Example 50.

mp. 113°–114° C. (2-propanol) colorless needles

Elemental analysis (%); as $C_{22}H_{22}F_3$ $N_3$ O

Calculated; C: 65.82 H: 5.52 N: 10.47

Found C: 65.68 H: 5.56 N: 10.62

The starting material, 1-(4-trifluoromethylphenyl)-3-(3-pyridyl)-2-imidazolidinone was synthesized from N-methoxycarbonyl-N-4-trifluoromethylphenylglycine similarly to Referential example 3 (A) and (B) and Example 17-A.

(EXAMPLE 54)

1-[4-(1-Phenylmethyl)-1,2,5,6-tetrahydropyridyl]-3-(2-propinyl)-2-imidazolidinone

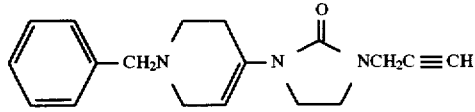

Using 1-(2-propynyl)-3-(4-pyridyl)-2-imidazolidinone as a starting material in place of 1-(2-chlorophenyl)-3-(3-pyridyl)-2-imidazolidinone, title compound was synthesized similarly to Example 50.

mp. 83°–84° C. (diisopropyl ether) colorless needles

Elemental analysis (%); As $C_{18}H_{21}N_3O$

Calculated; C: 73.19 H: 7.17 N: 14.23

Found; C: 73.23 H: 7.13 N: 14.21

The starting raw material, 1-(2-propynyl)-3-(4-pyridyl)-2-imidazolidinone was synthesized similarly to Referential example 1, using 1-(4-pyridyl)-2-imidazolidinone as material and using 3-bromopropyne in place of 4-fluoronitrobenzene.

(EXAMPLE 55)

1-[3-(1-Phenylmethyl)-1,2,5,6-tetrahydropyridyl]-3-(2-propynyl)- 2-imidazolidinone

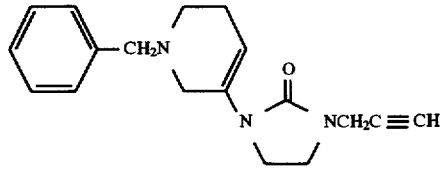

Using 1-(2-propynyl)-3-(3-pyridyl)-2-imidazolidinone as material in place 1-(2-chlorophenyl)-3-(3-pyridyl-2-imidazolidinone, title compound was synthesized similarly to Example 50. Pale yellow oil.

$^1$H-NMR (TMS in $CDCl_3$, 400 Mz)

δ 2.12–2.16 (3H, m), 3.43 (2H, t, J=6.0 Hz), 3.36 (1H, d, J=9.8 Hz), 3.38 (1H, d, J=7.8 Hz), 3.45 (1H, d, J=7.8 Hz), 3.47 (1H, d, J=9.8 Hz), 3.57 (4H, s), 3.93 (2H, d, J=3.9 Hz), 4.90 (1H, t, J=3.9 Hz), 7.15–7.30 (5H, m), 7.63 (1H, d, J=7.8 Hz), 8.51–8.55 (2H, m)

H. R. M6s; As $C_{18}H_{21}N_3O$

Calculated; m/Z: 295. 1685 Found; m/z: 295. 1709

The starting material, 1-(2-propynyl)-3-(3-pyridyl)-2-imidazolidinone was synthesized similarly to Referential example 1, using 1-(3-pyridyl)-2-imidazolidinone as material and using 3-bromopropyne in place of 4-fluoronitrobenzene.

(EXAMPLE 56)

1-[3-(1-Phenylmethyl)-1,2,5,6-tetrahydropyridyl]-3-(4-methoxyphenylmethyl)-2-imidazolidinone

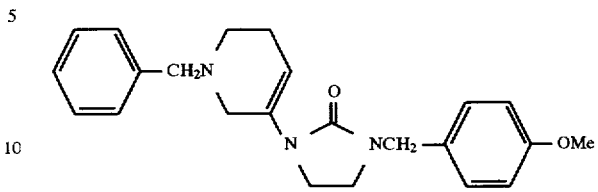

Using 1-(4-methoxyphenylmethyl)-3-(3-pyridyl)-2-imidazolidinone as material in place of 1-(2-chlorophenyl)-3-(3-pyridyl)-2-imidazlidinione, title compound was synthesized similarly to Example 50. Colorless oil.

$^1$H-NMR (TMS in $CDCl_3$, 400 MHz)

δ 2.20–2.33 (2H, m), 3.50 (2H, t, J=5.9 Hz), 3.19 (1H, d, J=9.8 Hz), 3.21 (1H, d, J=8.3 Hz), 3.45 (1H, d, J=8.3 Hz), 3.47 (1H, d, J=9.8 Hz), 3.66 (2H, s), 3.71 (2H, d, J=1.5 Hz),2.80 (3H, s), 4.29 (2H, s), 4.92 (1H, brs), 6.85 (2H, d, J=8.6 Hz), 7.18 (2H, d, J=8.6 Hz), 7.25–7.39 (5H, m)

H. R. Mass; As $C_{23}H_{27}N_3O_2$

Calculated: m/Z: 377. 2103 Found; m/z: 377. 2904

The starting material, 1-(4-methoxyphenylmethyl)-3-(3-pyridyl)-2-imidazolidinone was synthesized similarly to Referential example 1, using 1-(3-pyridyl)-2-imidazolidinone as a raw material and using 4-methoxyphenylmethylchlride in place of 4-fluoronitrobenzene.

(EXPERIMENTAL EXAMPLE 1)

In vitro biochemical test

1) Radioligand binding experiment to $M_1$ type muscarinic cholinergic receptor

Method: To a crude synaptosome membrane specimen prepared from all brains (except cerebellum and brain stem) of rat, [$^3$H]-pirenzepine ([$^3$H]-PZ, final concentration: 1 nM) and testing compound were added and the mixture was incubated for 60 minutes at 25° C. After stopped the reaction by filtered with suction, the radioactivity on filter was measured with liquid scintillation counter. The specific binding level of [$^3$H]-pirenzepine was determined by subtracting the non-specific binding level in the presence of atropine (1 μM) from total binding level. Putting the [$^3$H]-pirenzepine binding in the absence of testing compound on 100, the concentration of compound to decrease by 50% ($IC_{50}$ value) was made an index of the binding activity of compound to $M_1$ muscarinic receptor (refer to: J. A. D. M. Toner et al, Life Science, 1987, 40, 1981–1987).

2) Radioligand binding experiment to $M_2$ type muscarinic cholinergic receptor

Method: Similar procedures were conducted to the experiment on the affinity to $M_1$ receptor, except that the crude synaptosome membrane specimen was prepared from the brain stem (medulla oblongata-pons) of rat and and [$^3$H]-quinuclidyl benzoate ([$^3$H]-QNB, 0.1 nM) was used as a radioactive ligand.

3) Selectivity to $M_1$ receptor

This was determined from the ratio of $IC_{50}$ values of testing compound obtained from the binding experiments of $M_1$ and $M_2$ muscarinic receptors.

$$\text{Receptor selectivity} = \frac{IC_{50}(|^3H| - QNB)}{IC_{50}(|^3H| - PZ)}$$

TABLE 7

| No. of compound | $|^3H|$-PZ ($M_1$) $IC_{50}$ μM | $|^3H|$-QMB ($M_2$) $IC_{50}$ μM | $IC_{50}$ ($M_2$)/$C_{50}$($M_1$) |
|---|---|---|---|
| Example 4 | 0.53 | >6.00 | >11.3 |
| Example 17 | 0.37 | >6.00 | >16.2 |

Results: Table 7 shows the affinity and selectivity of the inventive compounds to $M_1$ and $M_2$ receptors. $IC_{50}$ substitution of $[^3H]$-PZ denotes the affinity of $M_1$ receptor and $IC_{50}$ substitution of $|^3H|$-QNB the affinity to $M_2$ receptor. It is shown that the higher the ratio of $M_2/M_1$, the higher the selectivity to $M_1$ receptor.

The results showed that the inventive compounds had potent affinity and remarkable specificity to the central $M_1$ muscarinic receptor.

(EXPERIMENTAL EXAMPLE 2)

In vivo pharmacological test

Testing on the pirenzepine-induced amnesia

For the experiment animals, Std:ddy strain male mice with body weight of 24 to 33 g (age in week: 5) (Nippon SLC) were used. For the device, a step-through type passive avoidance apparatus (made by Ohara Medical Co., Ltd.) consisting of two light and dark rooms was used. In the acquisition trial, mouse was placed in the light room and, 10 seconds later, the partitive guillotine door was opened. As soon as the mouse moved into the dark room, the guillotine door was closed and electric shock of 43 to 44 V was given for 1 second through the metal grid bars of the floor. The retention trial was conducted 24 hours later since then. In the retention trial, mouse was placed again in the light room and the time until they moved into the dark room was measured for at maximum 300 seconds as a reaction latency; for mouse exhibited longer latency than it, the time was made to be 300 seconds. The induction of amnesia was performed by fixing a mouse at prone position without anesthetization at 20 minutes before learning acquisition trial and injecting pirenzepine (10 μg/2 μl/mouse bilaterally into cerebral ventricles using a microsyringe. Moreover, a group not to administered with pirenzepine before acquisition trial (non-amnesia comparison group) was also provided. The testing compound was administered orally at 60 minutes before acquisition trial. The improvement rate was calculated according to following equation and the results are shown in Table 8 (refer to: M. P. Callfield et al, J. Pharm. Pharmacol.) 1983, 35, 131–132).

Improvement rate =

$$\frac{\text{Latency of compound-administered amnesia group} - \text{latency of pirenzepine-treated group}}{\text{Latency of non-amnesia comparison group} - \text{latency of pirenzepine-treated group}} \times 100$$

TABLE 8

| Compound | Dose (mg/kg) | Number of animals used | Reaction latency Mean ± S.E. | Improvement rate (%) |
|---|---|---|---|---|
| Non-treated | — | 8 | 149.5 ± 44.1 | |
| Pirenzepine-treated mouse | — | 8 | 10.4 ± 2.0 | |
| Example 4 | 3 | 8 | 71.1 ± 30.2‡ | 43.6 |
| Non-treated | — | 13 | 221.6 ± 27.9 | |
| Pirenzepine-treated mouse | — | 13 | 37.9 ± 18.3 | |
| Example 17 | 1 | 13 | 189.9 ± 52.8‡‡ | 82.7 |
|  | 3 | 13 | 164.2 ± 37.5‡‡ | 68.8 |

‡: p < 0.05
‡‡: p < 0.01 With significant differences against pirenzepine-treated mice Results: Table 8 shows the improvement effect of the inventive compounds on the pirenzepine-induced amnesia.

The reduction of the reaction latency of pirenzepine-treated mice relative to the group without treatment indicates that the decreased learning effect due to electric shock, that is, amnesia is caused. The extension of the reaction latency with compound therefore means the improved amnesia.

The results showed that the inventive compounds had very excellent improvement effect on the amnesia caused by the disturbance of central cholinergic nerves.

Utilizability in the industry

As described above, the inventive imidazolidinone derivatives have excellent functionally cholinergic activity, hence they are effective for the therapy of the disturbance of memory and yet useful as therapeutic drugs of senile dementia with high safety.

We claim:

1. An imidazolidinone represented by the formula (1)

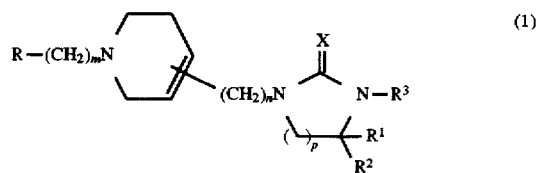

wherein R denotes a lower alkyl group which may be substituted by halogen, cyclic alkyl group having 3 to 7 carbons, or phenyl group, or naphthyl group, $R^1$ and $R^2$ denote identically or differently hydrogen atoms or lower alkyl groups, $R^3$ denotes a formula

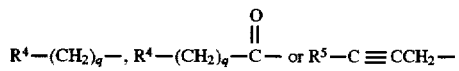

wherein $R^4$ denotes a lower alkyl group which may be substituted by halogen, cyclic alkyl group having 3 to 7 carbons, or phenyl group, or naphthyl group, q denotes 0 to 3, and $R^5$ denotes a hydrogen atom, m and n denote 0 to 3, p denotes 1, and X denotes an oxygen atom or sulfur atom, or salt thereof.

2. A composition, comprising an imidazolidinone represented by the formula (1)

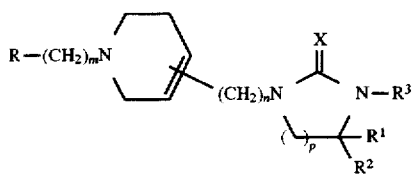

(1)

wherein R denotes a lower alkyl group which may be substituted by halogen, cyclic alkyl group having 3 to 7 carbons, or phenyl group, or naphthyl group, $R^1$ and $R^2$ denote identically or differently hydrogen atoms or lower alkyl groups, $R^3$ denotes a formula

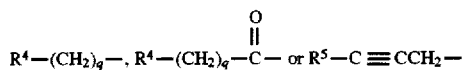

wherein $R^4$ denotes a lower alkyl group which may be substituted by halogen, cyclic alkyl group having 3 to 7 carbons, or phenyl group, or naphthyl group, q denotes 0 to 3, and $R^5$ denotes a hydrogen atom, m and n denote 0 to 3, p denotes 1, and X denotes an oxygen atom or sulfur atom, or salt thereof;
in an inert carrier.

3. The imidazolidinone derivative of claim 1, having the structure:

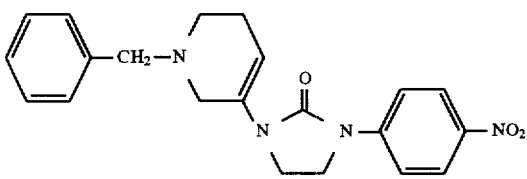

4. The imidazolidinone derivative of claim 1, having the structure:

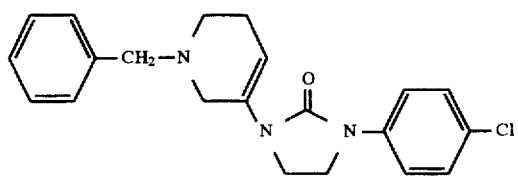

* * * * *